(12) United States Patent
Uibel et al.

(10) Patent No.: US 8,409,655 B2
(45) Date of Patent: Apr. 2, 2013

(54) PROCESS AND APPARATUS FOR PRODUCING THREE-DIMENSIONAL SHAPED CERAMIC BODIES

(75) Inventors: Krishna Uibel, Kempten (DE); Rainer Telle, Aachen (DE); Horst Fischer, Aachen (DE)

(73) Assignees: Horst Fischer, Aachen (DE); Rainer Telle, Aachen (DE); Joerg Erbert, Aachen (DE); Emre Oezkol, Aachen (DE)

( * ) Notice: Subject to any disclaimer, the term of this patent is extended or adjusted under 35 U.S.C. 154(b) by 764 days.

(21) Appl. No.: 12/225,712

(22) PCT Filed: Mar. 27, 2007

(86) PCT No.: PCT/EP2007/002693
§ 371 (c)(1),
(2), (4) Date: Oct. 21, 2009

(87) PCT Pub. No.: WO2007/112885
PCT Pub. Date: Oct. 11, 2007

(65) Prior Publication Data
US 2010/0040767 A1    Feb. 18, 2010

(30) Foreign Application Priority Data
Mar. 31, 2006 (DE) .......................... 10 2006 015 014

(51) Int. Cl.
*A61L 27/32* (2006.01)
(52) U.S. Cl. ....... 427/2.27; 427/287; 427/533; 427/555; 427/559
(58) Field of Classification Search ................ 427/2.27, 427/287, 559, 533, 555
See application file for complete search history.

(56) References Cited

U.S. PATENT DOCUMENTS

| 6,017,110 A | 1/2000 | Jackson |
| 6,336,699 B1 | 1/2002 | Sarkissian et al. |
| 2004/0165031 A1 | 8/2004 | Nishi et al. |

FOREIGN PATENT DOCUMENTS

JP    2003-531220 A    10/2003

OTHER PUBLICATIONS

Wang, et al., Abstract, "Rapid prototyping of ceramic components by slurry jet printing," Journal of the Chinese Ceramic Society, (2001), vol. 29, No. 4, pp. 344-349.
Zhao, et al., "Ink-jet printing of ceramic pillar arrays," Journal of Materials Science, (2002), vol. 37, No. 10, pp. 1987-1992.
Song, et al., Abstract, "Defects and prevention in ceramic components fabricated by inkjet printing," Journal of Materials Processing Technology, (2004), vol. 155-156, pp. 1286-1292.
Evans, et al., Abstract, "Combinatorial searches of inorganic materials using the ink-jet printer: science, philosophy and technology," Journal of the European Ceramic Society, (2001), vol. 21, No. 13, pp. 2291-2299.
Mott, et al., Abstract, "Zirconia/alumina functionally graded material made by ceramic ink jet printing," Materials Science and Engineering, (1999), vol. A271, No. 1-2, pp. 344-352.

*Primary Examiner* — Paul Marcantoni
(74) *Attorney, Agent, or Firm* — Tanya E. Harkins; Nath, Goldberg & Meyer

(57) ABSTRACT

A process for producing three-dimensional shaped ceramic bodies by layerwise printing of a suspension comprising the constituents required for formation of the shaped ceramic bodies by means of an inkjet printer in the desired two-dimensional shape onto a support material, drying and hardening of the layer composite formed, which is characterized in that printing is effected using a suspension comprising from 50 to 80% by weight of ceramic particles in a dispersion medium comprising an aqueous boehmite sol, at least one low molecular weight alcohol, at least one drying inhibitor and at least one organic fluidizer, and also an apparatus for carrying out this process are described.

38 Claims, No Drawings

PROCESS AND APPARATUS FOR PRODUCING THREE-DIMENSIONAL SHAPED CERAMIC BODIES

The present invention relates to a process for producing three-dimensional shaped ceramic bodies by layerwise printing of a suspension comprising the constituents required for formation of the shaped ceramic bodies by means of an inkjet printer in the desired two-dimensional shape onto a support material, drying and hardening of the layer composite formed, and also an apparatus for carrying out this process.

Conventional processes for producing three-dimensional shaped ceramic bodies generally comprise the use of tools such as pressing or casting molds matched to the shaped bodies to be produced. Although this method is suitable for producing a large number of identical three-dimensional shaped bodies, the process is disadvantageous when only small numbers of shaped bodies having different three-dimensional shapes are to be produced. This makes the production of prostheses for human bodies based on such three-dimensional shaped ceramic bodies difficult because these prostheses have to be adapted individually.

However, shaping methods which comprise direct construction of complex shaped bodies from geometrically small units by controlled deposition of material carried out under computer control proceeding from a three-dimensional computer model are also known. The important advantage compared to conventional shaping methods is the free shaping, with additional support constructions also being able to be employed if appropriate. Computer-controlled production processes of this type are also referred to as solid free form fabrication or rapid prototyping. While the latter encompasses microextrusion, stereolithography, laser generation and the like, inkjet printing and selective laser sintering have also become known for the production of free-formed solid bodies (SFF).

Thus, EP 0 847 314 B1 describes a process for producing a sintered structure on a substrate, in which a liquid laden with particles is applied by means of an inkjet printer to the substrate, after which the liquid is evaporated and the remaining particles are sintered. In this process, sintering of the particles is carried out layerwise by means of a laser. This method is unsatisfactory insofar as the necessity of layerwise sintering of the particles by means of a laser makes the use of complicated apparatuses necessary.

In J. Am. Ceram. Soc., 85 (2002), 2113-2115, X. Zhao et al. describe the production of vertical ceramic walls by layerwise printing of a printing liquid containing ceramic particles by means of an inkjet printer. The printing liquid used here comprises zirconium dioxide particles, a dispersant, isopropyl alcohol, octane and wax. After printing of this printing liquid in the form of individual layers by means of the inkjet printer, with the printing table being lowered in the z direction each time, the printed three-dimensional specimens are dried and then pyrolyzed at elevated temperature to remove the organic constituents. The $ZrO_2$ ceramic particles are subsequently sintered.

However, it has been found that this process does not appear suitable for mass production of three-dimensional shaped ceramic bodies because the printing liquid used does not have the necessary stability, with the suspended ceramic particles settling, blocking the nozzles of the printing head of the inkjet printer and ultimately preventing uniform deposition of the ceramic material in the form of the desired layers and thus the three-dimensional shaped body. As a result, the shaped bodies after pyrolysis and sintering do not have the desired dimensional accuracy and uniform density and thus strength.

It is an object of the present invention to provide a process and an apparatus by means of which these disadvantages can be overcome and which make it possible, in a simple manner, to produce three-dimensional shaped ceramic bodies of various shapes with high dimensional accuracy and constant mechanical properties and at the same time solve the problem of stability and the state of dispersion and the suitability of the printing liquid containing suspended ceramic particles for use in an inkjet printer.

It has now surprisingly been found that this object can be achieved by the suspension used for printing by means of an inkjet printer comprising a dispersion medium and ceramic particles suspended therein, with the dispersion medium comprising an aqueous boehmite sol as essential constituent.

The invention accordingly provides the process as claimed in claim 1 and an apparatus for carrying out the process.

The dependent claims relate to preferred embodiments of these subjects of the invention.

The invention therefore provides, in particular, a process for producing three-dimensional shaped ceramic bodies by layerwise printing of a suspension comprising the constituents required for formation of the shaped ceramic bodies by means of an inkjet printer in the desired two-dimensional shape onto a support material, drying and hardening of the layer composite formed, which is characterized in that printing is effected using a suspension comprising from 50 to 80% by weight of ceramic particles in a dispersion medium comprising an aqueous boehmite sol, at least one low molecular weight alcohol, at least one drying inhibitor and at least one organic fluidizer.

It has surprisingly been found that the suspension used as printing liquid in the process of the invention displays very good stability and even at high solids contents displays virtually no tendency of the ceramic particles to settle. If necessary, the ceramic particles can be redispersed by simple shaking. Furthermore, the suspension used according to the invention has a viscosity suitable for the present process and good wetting and drying behavior even at high solids contents, namely a content of ceramic particles of from 50 to 80% by weight. In contrast to the teachings of the known prior art, it is possible by means of this suspension and the process of the invention to produce any three-dimensional shaped ceramic bodies having a high dimensional accuracy and uniform mechanical properties without formation of voids in the sintered shaped ceramic bodies.

In a preferred embodiment, the solids content of the boehmite sol present in the dispersion medium of the printing suspension according to the invention is from 0.001 to 2% by weight, more preferably from 0.001 to 1% by weight and even more preferably from 0.01 to 0.5% by weight. Here, the boehmite sol contains nanocrystalline boehmite particles and dissolved aluminum hydrate.

The nanocrystalline boehmite particles (AlO(OH)) preferably have a particle size of from 3 to 20 nm, more preferably from 4 to 5 nm, and have, particularly advantageously, a ratio of length to width (aspect ratio) of from 1.4:1 to 2.2:1, as a result of which the ceramic particles can be kept in suspension in a particularly stable manner.

As dissolved aluminum hydrate, the boehmite sol present according to the invention in the dispersion medium comprises the neutral or ionic compounds of the following formulae $[Al(H_2O)_6]^{3+}$, $[Al(H_2O)_5OH]^{2+}$, $[Al(H_2O)_4(OH)_2]^+$, $Al(OH)_3(aq)$, $[Al(OH)_4]^-$.

According to the invention, it is particularly advantageous for the boehmite sol to have a pH of from 1.7 to 11, preferably from 4 to 10 and even more preferably from 5 to 8. At a pH of the boehmite sol within this range, very good colloidal suspension of the ceramic particles can be maintained in a stable manner while at the same time achieving good pumpability and printability of the suspension.

In a further preferred embodiment of the invention, the dispersion medium comprises from 48 to 88% by weight of boehmite sol, from 50 to 20% by weight of low molecular weight alcohol, from 5 to 20% by weight of drying inhibitor and from 2 to 12% by weight of organic fluidizer or an organic dispersant.

The dispersion medium preferably comprises methanol, ethanol, propanol, isopropanol or mixtures thereof as low molecular weight alcohol and a polyhydric alcohol, a long-chain hydrocarbon or mixtures thereof, for example glycerol and/or ethylene glycol, as drying inhibitor. As organic fluidizer or organic dispersant, the dispersion medium preferably contains a synthetic organic polyelectrolyte and/or a carboxylic acid preparation. As synthetic organic polyelectrolyte, preference is given to polyacrylic acid and/or polymethacrylic acid having a weight average molecular weight of from 4000 to 6000, with these acids preferably being present in the form of an alkali metal or ammonium salt. These preferred synthetic organic polyelectrolytes give a suspension which does not foam and, owing to the presence of these organic fluidizers, can very readily be applied layerwise to a substrate material by means of a conventional inkjet printer. Particular preference is given to the polyacrylic acids in the form of the ammonium salts which can be obtained from Zschimmer & Schwarz under the names Dolapix CE64, Dolapix PC75 and Dolapix ET85.

In a further preferred embodiment, the dispersion medium comprises from 62 to 91% by weight of boehmite sol, from 5 to 15% by weight of ethanol, from 2 to 15% by weight of glycerol and/or ethylene glycol and from 2 to 8% by weight of polyacrylic acid and/or polymethacrylic acid in the form of the ammonium salt.

In an advantageous embodiment of the invention, the suspension used as printing liquid comprises ceramic particles which comprise pure $Al_2O_3$, pure $ZrO_2$, pure $Al_2O_3$—$ZrO_2$, pure $Si_3N_4$, $Al_2O_3$ stabilized with boehmite, $ZrO_2$ stabilized with $Y_2O_3$, $HfO_2$, $CeO_2$, MgO and/or CaO, $Al_2O_3$—$ZrO_2$ stabilized with $Y_2O_3$, $HfO_2$, $CeO_2$, MgO and/or CaO, $Si_3N_4$ stabilized with $Al_2O_3$, $Y_2O_3$, $Fe_2O_3$ and/or further rare earth oxides, or mixtures thereof.

The $Al_2O_3$—$ZrO_2$ mixed ceramic which may be stabilized with $Y_2O_3$, $HfO_2$, $CeO_2$, MgO and/or CaO preferably comprises from 30 to 70% by weight of $Al_2O_3$ and correspondingly from 70 to 30% by weight of $ZrO_2$. Preference is given to a $Y_2O_3$-stabilized $ZrO_2$ which can be obtained from Tosoh, Tokyo, under the name TZ-3YS-E.

According to the invention, particular preference is given to the suspension containing from 60 to 70% by weight of ceramic particles. Here, the particle size of the ceramic particles has to be smaller than the opening of the nozzles of the printing head of the inkjet printer used and the feed lines and is preferably in the region of a d90 of from 0.01 to 3 μm, more preferably from 0.5 to 1.5 μm.

It is advantageous for the suspension of the ceramic particles in the dispersion medium according to the invention to have a pH of from 4 to 11, preferably from 7 to 9, and a viscosity measured at 25° C. and shear rates of $\gamma>400$ of from 5 to 25 mPas and a viscosity measured at low shear rates of $\gamma<50$ of from 100 to 500 mPas since the suspension can at this viscosity be readily conveyed and ejected by means of the pumps of conventional inkjet printers through the printing heads and printing nozzles of these conventional inkjet printers.

In the process of the invention, the layers forming the desired three-dimensional shaped ceramic bodies are printed onto a planar support material, for example a graphite plate, a platinum sheet, a ceramic or a glass-ceramic having an open porosity of from 0 to 10%.

In a further embodiment of the invention, it is possible to print the layers forming the three-dimensional shaped ceramic body onto a support material onto which one or more layers which have defined dimensions and can be removed during hardening of the layer composite have previously been printed using a suspension comprising a material which vaporizes during hardening of the layer composite in the dispersion medium indicated. This makes it possible to form a three-dimensional shaped ceramic body which has specific recesses, openings and the like by means of which it can be fitted accurately and joined to a corresponding counterpiece, for example the metal part or even a ceramic part of a tooth implant in which the three-dimensional shaped body produced according to the invention serves as tooth crown.

In a preferred embodiment of the invention, one or more layers which have defined dimensions and can be removed during hardening of the layer composite are printed in addition to or between the layers printed by means of the first printing head by means of a second printing head using a suspension comprising a material which vaporizes during hardening of the layer composite in the dispersion medium indicated. This makes it possible for a three-dimensional shaped ceramic body which has recesses, undercuts, etc., in the desired places so that it can with the aid of these be fitted to the counterpiece to be joined on to be produced in a single printing step.

As vaporizing material in this embodiment of the invention, preference is given to using a material which vaporizes at a temperature above 200° C. or pyrolizes in the presence of oxygen at a temperature above 400° C.

Even though the suspension or printing liquid used in the process of the invention displays a very low tendency for the ceramic particles to settle or adhere to the nozzles of the printing head of the inkjet printer, the nozzles of the printing head are, in a preferred embodiment of the invention, cleaned by means of a cleaning liquid comprising water, a low molecular weight alcohol and/or a polyhydric alcohol after printing of one or more layers. The cleaning liquid preferably comprises a mixture of water, ethanol and at least one polyhydric alcohol in a weight ratio of water:ethanol:polyhydric alcohol of 6-10:1-4:1-3, preferably 8:1:1.

The cleaning of the nozzles of the printing head is advantageously carried out in such a way that the cleaning liquid penetrates into the nozzles and the antechambers of the nozzles. This penetration of the cleaning liquid into the nozzles and the antechambers of the nozzles can be effected by means of elevated external pressure or subatmospheric pressure in the printing cartridge containing the suspension. This can be achieved, for example, by the internal pressure of the gas phase of the printing cartridges being set to a value which is from 2 to 100 mbar (corresponding to from 200 to 10 000 Pa) below, preferably from 2 to 25 mbar (corresponding to from 200 to 2500 Pa) below, atmospheric pressure and is, in a particularly preferred variant, controlled as a function of the level of fill of the suspension in the printing cartridge so that the pressure difference in the interior of the printing cartridge remains constant as a function of the level of fill of the suspension in the printing cartridge.

In a further preferred embodiment of the invention, the cleaning of the nozzles of the printing head is carried out by means of a body which is impregnated with the cleaning liquid and is periodically wiped over the cleaning head in the region of the nozzles under a contact pressure of from 0.01 to 1 N/mm$^2$, preferably from 0.02 to 0.05 N/mm$^2$. This body is preferably an open-pored foam or a microfiber cloth or even a combination thereof, i.e., for example, an open-pored foam over which a microfiber cloth is stretched. This body has, for example, the shape of a cylinder and is pressed while being rotated around its longitudinal axis under the indicated contact pressure against the nozzles of the printing head and conveyed past them. In a preferred embodiment, the printing head is conveyed past this cleaning device on reaching its end position or any desired position.

Furthermore, it is possible to carry out the cleaning of the nozzles of the printing head under the action of ultrasound, and this measure can also be combined with mechanical cleaning using the body impregnated with the cleaning liquid. The cleaning of the nozzles of the printing head is preferably carried out periodically under the action of ultrasound between the pressure cycles in the printing cartridge or at the printing head.

After printing, the printed layers are dried at a temperature of from 65° C. to 105° C., with each individual layer preferably being dried after application. This is preferably effected by each individual printed layer being dried in the printing region of the inkjet printer by heating to a temperature in the range from 65° C. to 105° C., preferably from 68° C. to 85° C., if appropriate using a fan, with application of reduced pressure or with convective flow to remove the vapor of the liquid. The drying of these layers can also be effected by irradiation with a halogen lamp, an infrared lamp, by means of ion radiation, laser radiation or using heating elements arranged in the printing region.

The printing of the suspensions is carried out so that the individual layers of the ceramic material after drying have a thickness of from 1 μm to 30 μm, preferably from 0.05 μm to 10 μm, and any individual layers of the material which vaporizes during hardening of the layer composite which have been printed on have a thickness of from 0.05 μm to 5 μm.

After drying of the last layer, the dried layer composite obtained in this way is hardened by sintering of the ceramic material, with preference being given to storing the layer composite obtained after printing at, if appropriate, elevated temperature in a drying oven, for example at a temperature of about 80° C. The hardening of the resulting layer composite of the ceramic material to form the three-dimensional shaped ceramic body is preferably effected by sintering at a temperature of from 800° to 1500° C. Sintering is preferably carried out to a sintered density of 100% of the theoretical density, preferably up to 98% of this density.

It has been found that use of the process of the invention makes it possible to produce, with high dimensional accuracy, three-dimensional shaped ceramic bodies which have no drying cracks, display no detachment of the individual layers and are outstandingly suitable for producing medical ceramic prostheses.

The process of the invention is therefore directed, in particular, at the production of medical ceramic prostheses, in particular prostheses in the region of the body, the limbs and the head, the face, the oral cavity, of tooth implants, tooth inlays, tooth crowns and tooth bridges.

The invention further provides an apparatus for carrying out the process, which is characterized by a conventional, computer-controlled inkjet printer having a support for the support material which can be moved vertically in the z direction, can be lowered by one layer height at a time under computer control and can be moved in the y direction and, if appropriate, in the x direction (the direction of movement of the printing head), a drying facility in the printing region and a cleaning system for the nozzles of the printing head.

The inkjet printer is preferably a commercial drop-on demand printer as can be obtained, for example, from the Hewlet Packard Company which has been modified by installation of a drying facility in the printing region and a cleaning system for the nozzles of the printing head. The cleaning system of this apparatus preferably comprises a body which can be impregnated with the cleaning liquid and can be brought into contact with the nozzles of the printing head under pressure in the cleaning step. The body which can be impregnated with the cleaning liquid preferably has the form of a cylinder of an open-pored foam over which the printing nozzles of the printing head are conveyed under pressure in cleaning contact during the cleaning step. The foam cylinder can preferably be rotated about its longitudinal axis and dips into the cleaning liquid on its side facing away from the printing head. It is advantageous here for the axis of the foam cylinder to run parallel to the printing direction of the inkjet printer, i.e. the direction of movement of the printing head (x direction) or perpendicular thereto (y direction).

In a preferred embodiment of the apparatus of the invention, a wiping roller to remove excess cleaning liquid is provided between the point where the foam cylinder leaves the cleaning liquid and the point at which it contacts the pressure head of the inkjet printer.

Furthermore, the cleaning system of the apparatus of the invention can comprise an ultrasonic bath containing the cleaning liquid into which the printing nozzles of the printing head can be lowered. The ultrasonic bath of this embodiment is preferably located in the region of the park position of the printing head.

When the process of the invention is carried out in practice, the precise shape of the three-dimensional shaped ceramic body to be produced is firstly generated on a computer, for example by scanning a model. For example, the data required for the shaped body to be formed can be set up on a commercial computer by means of a software program such as Microsoft WORD. The x and y dimensions of the future three-dimensional shaped body are given by the two-dimensional representation of the object set up in this WORD document in the form of the individual layers to be printed. The three-dimensionality of the shaped body is produced by repeated printing of the individual layers having the appropriate dimensions.

The printing cartridges are subsequently filled with the suspension to be printed on, after which the printing head is conveyed in accordance with the control program over the support material and the suspension is printed on in the desired shape in the form of a layer. This layer is subsequently dried before application of the next layer. These measures are continued while at the same time lowering the support for the support material by one layer height at a time until the green three-dimensional shaped ceramic body has been produced. This shaped body is subsequently, if appropriate after storage at 80° C. in a drying oven, sintered at the temperature required for full sintering of the ceramic material and gives the desired three-dimensional shaped ceramic body with high surface accuracy and surface quality.

This mode of operation according to the invention makes it readily possible to print more than 10 000 printing cycles, i.e. more than 10 000 layers having the desired two-dimensional shape, without the nozzles of the printer becoming blocked.

The following examples serve to illustrate the invention.

EXAMPLE

To produce the boehmite sol used in the dispersion medium according to the invention, 700 ml of water are brought to a pH of 2 by addition of 65% strength nitric acid. The mixture is heated to 80° C. and 2.1 g of boehmite (Dispersal P2, from Sasol, Hamburg) are added and the mixture is stirred for 10 minutes. The mixture is allowed to cool to room temperature, 25% strength ammonia is added to a pH of 8.5 and the aqueous boehmite sol obtained is stored in a polyethylene bottle.

To produce the actual printing dispersion, 150 g of the boehmite sol produced as described above are mixed with 30 g of 85% strength glycerol, 4.5 g of an ammonium polyacrylate (Dolapix CE64, from Zschimmer & Schwarz, Lahnstein) and 11 g of an ammonium polyacryate (Dolapix PC75, from Zschimmer & Schwarz, Lahnstein) are added and the mixture is stirred for 30 seconds. 450 g of zirconium dioxide stabilized with yttrium oxide (TZ-3YS-E from Tosoh, Tokyo) are subsequently added and the mixture is mixed in a dispersing apparatus (Ultra-Turrax T25 Basic, IKA-Werke, Staufen) provided with the appropriate dispersing head (S25N-10G, IKA-Werke, Staufen) at from 6500 to 13 500 min$^{-1}$ for one minute, with 25 g of ethanol being added during mixing. The mixture is subsequently dispersed at 24 000 min$^{-1}$ for a further 2 minutes and the suspension obtained is introduced into an empty printer cartridge.

To produce a suspension for printing layers which are removed during hardening of the layer composite, 85 g of distilled water are placed in a 250 ml polyethylene bottle and 8.5 g of glycerol and 2.5 g of ammonium polyacrylate (Dolapix ET85, Zschimmer & Schwarz, Lahnstein) are added. 1.5 g of polyethylene glycol 400, 34 g of ethanol and 38.5 g of carbon black (Arosperse 15, Degussa, Frankfurt) are then added. 200-250 g of $Al_2O_3$ milling media having a diameter of 5 mm are added and the material is homogenized on rollers for 40-45 hours. The milling media are then removed and the suspension obtained is introduced into an empty printer cartridge.

A three-dimensional shaped body which forms the accurately dimensioned recess in the three-dimensional shaped ceramic body which is ultimately to be produced is firstly printed onto a support material comprising a graphite plate using the abovementioned second suspension. This is carried out using an inkjet printer of the drop-on-demand type which has been modified so that it allows computer-controlled lowering of the printing table in the z direction so as to make layerwise build up of the three-dimensional shaped body possible. The printer cartridges containing the printing suspensions indicated are installed and the inkjet printer is operated in the usual way, with the printing head being conveyed in the usual way under computer control in the x direction over the support material which is moved in the y direction by the printer control. The positioning accuracy in this mode of operation is 20 μm.

Each applied layer is subsequently dried by means of a halogen lamp whose light is focused in the printing region by means of convex optical lenses. At the same time, a fan over the substrate produces convection and thus accelerated drying. During this procedure, the temperature of the support material and the layers applied thereto are kept below 130° C., preferably at about 80° C. After construction of the three-dimensional body of the material which vaporizes during hardening of the layer composite, the printer cartridge is replaced by a printer cartridge containing the first-named suspension which contains the ceramic particles of zirconium dioxide stabilized with yttrium oxide and a second three-dimensional shaped body based on ceramic particles and having the desired shape is printed layerwise in the same way onto the first three-dimensional shaped body, with the layers each being dried in the manner indicated.

After manufacture of the three-dimensional shaped body, this is dried briefly at a temperature of about 80° C. in a drying oven and then heated to a temperature of about 400° C. in the presence of oxygen in order to vaporize or pyrolize the organic components still present. The resulting three-dimensional shaped body having the recess corresponding to the first three-dimensional shaped body based on the material which vaporizes during hardening of the layer composite is then sintered at a temperature of 1400° C. to form the desired three-dimensional shaped ceramic body having high dimensional accuracy and surface quality.

This shaped ceramic body has a density of about 98% of the theoretical sintered density, displays no cracks, has a high flexural strength and is therefore highly suitable as medical ceramic prostheses, for example as crown of a tooth implant.

The invention claimed is:

1. A process for producing three-dimensional shaped ceramic bodies by layered printing of a suspension comprising the constituents required for formation of the shaped ceramic bodies by means of an inkjet printer into a two-dimensional shape onto a support material, drying and hardening of the layer composite formed, characterized in that printing is effected using a suspension comprising from 50 to 80% by weight of ceramic particles in a dispersion medium comprising an aqueous boehmite sol, at least one low molecular weight alcohol selected from the group consisting of methanol, ethanol, propanol, isopropanol or mixtures thereof, at least one drying inhibitor and at least one organic fluidizer.

2. The process as claimed in claim 1, characterized in that the boehmite sol has a solids content of from 0.0001 to 2% by weight.

3. The process as claimed in claim 1, characterized in that the boehmite sol comprises nanocrystalline boehmite particles and dissolved aluminum hydrate.

4. The process as claimed in claim 1, characterized in that the nanocrystalline boehmite particles have a particle size of from 3 to 20 nm.

5. The process as claimed in claim 1, characterized in that the nanocrystalline boehmite particles have a ratio of length to width of from 1.4:1 to 2.2:1.

6. The process as claimed in claim 1, characterized in that the boehmite sol contains $[Al(H_2O)_6]^{3+}$, $[Al(H_2O)_5OH]^{2+}$, $[Al(H_2O)_4(OH)_2]^{30}$, $Al(OH)_3(aq)$, $[Al(OH)_4]^{31}$ and/or $Al_{13}$ ions as dissolved aluminum hydrate.

7. The process as claimed in claim 1, characterized in that the boehmite sol has a pH of from 1.7 to 11.

8. The process as claimed in claim 1, characterized in that the dispersion medium comprises from 48 to 88% by weight of boehmite sol, from 5 to 20% by weight of the low molecular weight alcohol, from 5 to 20% by weight of the drying inhibitors and from 2 to 12% by weight of the organic fluidizers.

9. The process as claimed in claim 8, characterized in that the dispersion medium contains the low molecular weight alcohol, a polyhydric alcohol, a long-chain hydrocarbon selected from the group consisting of glycerol, ethylene glycol and mixtures thereof as the drying inhibitor and an organic polyelectrolyte and/or a carboxylic acid as the organic fluidizer.

10. The process as claimed in claim 9, characterized in that the dispersion medium contains polyacrylic acid and/or polymethacrylic acid having a weight average molecular weight of from 4000 to 6000.

11. The process as claimed in claim 1, characterized in that the dispersion medium comprises from 62 to 91% by weight of boehmite sol, from 5 to 15% by weight of ethanol, from 2 to 15% by weight of glycerol and/or ethylene glycol and from 2 to 8% by weight of organic fluidizers.

12. The process as claimed in claim 1, characterized in that the ceramic particles comprise $Al_2O_3$, $ZrO_2$, $Al_2O_3$—$ZrO_2$, $Si_3N_4$, $Al_2O_3$ stabilized with boehmite, $ZrO_2$ stabilized with $Y_2O_3$, $HfO_2$, $CeO_2$, MgO and/or CaO, $Al_2O_3$—$ZrO_2$ stabilized with $Y_2O_3$, $HfO_2$, $CeO_2$, MgO and/or CaO, $Si_3N_4$ stabilized with $Al_2O_3$, $Y2O3$, $Fe2O3$ and/or further rare earth oxides, or mixtures thereof.

13. The process as claimed in claim 12, characterized in that the $Al_2O_3$—$ZrO_2$ mixed ceramic which may be stabilized with $Y_2O_3$, $HfO_2$, $CeO_2$, MgO and/or CaO comprises from 30 to 70% by weight of $Al_2O3$ and correspondingly from 70 to 30% by weight of $ZrO_2$.

14. The process as claimed in claim 1, characterized in that the ceramic particles are present in an amount of from 60 to 70% by weight in the suspension.

15. The process as claimed in claim 1, characterized in that the particle size of the ceramic particles is smaller than the opening of the nozzles of the printing head and the feed lines and is in the region of a d90 of from 0.01 to 3 μm.

16. The process as claimed in claim 1, characterized in that the suspension has a pH of from 4 to 11, and a viscosity at 25° C. of from 5 to 25 mPas at shear rates of $\gamma>400$ and from 100 to 500 mPas at low shear rates of $\gamma<50$.

17. The process as claimed in claim 1, characterized in that the layers are printed onto a planar support material.

18. The process as claimed in claim 17, characterized in that the layers are printed onto a graphite plate, a platinum sheet, a ceramic or a glass-ceramic having an open porosity of from 0 to 10% as support material.

19. The process as claimed in at least one of the preceding claims, characterized in that the layers are printed onto a support material onto which one or more layers which can be removed during hardening of the layer composite have previously been printed using a suspension comprising a material which vaporizes during hardening of the layer composite in the dispersion medium indicated.

20. The process as claimed in claim 1, characterized in that one or more layers which can be removed during hardening of the layer composite are printed between or in addition to the layers printed by means of the first printing head by means of a second printing head using a suspension comprising a material which vaporizes during hardening of the layer composite in the dispersion medium indicated.

21. The process as claimed in claim 19, characterized in that a material which vaporizes at a temperature above 200° C. or pyrolizes in the presence of oxygen at a temperature above 400° C. is used as material which vaporizes during hardening of the layer composite.

22. The process as claimed in claim 1, characterized in that the nozzles of the printing head are cleaned by means of a cleaning liquid comprising water, a low molecular weight alcohol selected from the group consisting of methanol, ethanol, propanol, isopropanol or mixtures thereof and a polyhydric alcohol after printing of one or more layers.

23. The process as claimed in claim 22, characterized in that a mixture of water, ethanol and at least one polyhydric alcohol in a weight ratio of water:ethanol:polyhydric alcohol of (6 10):(1 4):(1-3), is used as cleaning liquid.

24. The process as claimed in claim 1, characterized in that cleaning of the nozzles of the printing head is carried out so that the cleaning liquid penetrates into the nozzles and the antechambers of the nozzles.

25. The process as claimed in claim 24, characterized in that the penetration of the cleaning liquid into the nozzles and the antechambers of the nozzles is under increased external atmospheric pressure or subatmospheric pressure in the pressure cartridge containing the suspension.

26. The process as claimed in claim 25, characterized in that the cleaning of the nozzles of the printing head is effected by means of a body which is impregnated with the cleaning liquid and is conveyed over the printing head in the region of the nozzles at a contact pressure of from 0.01 to 1 N/mm2.

27. The process as claimed in claim 1, characterized in that the cleaning of the nozzles of the printed head is carried out under the action of ultrasound.

28. The process as claimed in claim 27, characterized in that cleaning of the nozzles of the printing head is carried out under the action of ultrasound between the pressure cycles in the printing cartridge or at the printing head.

29. The process as claimed in claim 1, characterized in that the printed layers are dried at a temperature of from 65 to 105° C.

30. The process as claimed in claim 29, characterized in that each individual layer is dried after printing.

31. The process as claimed in claim 30, characterized in that each individual printed layer is dried in the printing region of the inkjet printer by heating to a temperature in the range from 65 to 105° C., optionally using a fan, application of a reduced atmospheric pressure or convection flow to remove the vapor of the liquid.

32. The process as claimed in claim 31, characterized in that heating is by irradiation with a halogen lamp, an infrared lamp, ion radiation, laser radiation or using heating elements located in the printing region.

33. The process as claimed in claim 1, characterized in that the individual printed layers of the ceramic material have a thickness of from 1 μm to 30 μm, after drying and the individual printed layers of the material which vaporizes during hardening of the layer composite have a thickness of from 0.05 μm to 5 μm.

34. The process as claimed in claim 1, characterized in that the hardening of the dried layer composite is optionally, after storage at about 80° C. in a drying oven, by sintering of the ceramic material.

35. The process as claimed in claim 34, characterized in that sintering is carried out at a temperature of from 800° C. to 1500° C.

36. The process as claimed in claim 34, characterized in that sintering is carried out to a sintered density of 100% of the theoretical density.

37. The process as claimed in claim 1, characterized in that the three-dimensional shaped ceramic bodies are medical ceramic prostheses prostheses in for a region of the body selected from the group consisting of limbs, head, face, and oral cavity.

38. The process as claimed in claim 1, characterized in that the three-dimensional shaped ceramic bodies are ceramic prostheses selected from the group consisting of tooth implants, tooth inlays, tooth crowns and tooth bridges.

* * * * *

UNITED STATES PATENT AND TRADEMARK OFFICE
CERTIFICATE OF CORRECTION

PATENT NO. : 8,409,655 B2
APPLICATION NO. : 12/225712
DATED : April 2, 2013
INVENTOR(S) : Krishna Uibel, Rainer Telle and Horst Fischer It is certified that error appears in the above-identified patent and that said Letters Patent is hereby corrected as shown below:

In the Claims

- Claim 6, column 8, Line 47, after [Al(H2O)4(OH)2]

Replace "30" with "+".

- Claim 6, column 8, Line 47, after [Al(OH)4]

Replace "31" with "-".

- Claim 37, column 10, Line 55, after "ceramic prostheses" and before "in for"

Delete "prostheses".

Signed and Sealed this
First Day of October, 2013

Teresa Stanek Rea
*Deputy Director of the United States Patent and Trademark Office*